(12) United States Patent
Meyer et al.

(10) Patent No.: US 6,437,206 B1
(45) Date of Patent: Aug. 20, 2002

(54) CATALYST AND PROCESSES FOR THE SELECTIVE HYDROGENATION OF UNSATURATED COMPOUNDS IN HYDROCARBON STREAMS

(75) Inventors: Gerald Meyer, Ludwigshafen; Ekkehard Schwab, Neustadt; Michael Hesse, Worms; Peter Trübenbach, Ludwigshafen; Hans-Joachim Müller, Grünstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/385,453

(22) Filed: Aug. 30, 1999

(30) Foreign Application Priority Data

Aug. 29, 1998 (DE) .......................................... 198 39 459

(51) Int. Cl.[7] .............................. C07C 5/08; B01J 23/42; B01J 23/44
(52) U.S. Cl. ...................... 585/260; 585/259; 585/258; 502/339; 502/330; 502/331; 502/345; 502/347
(58) Field of Search ................................ 502/339, 330, 502/331, 345, 347; 585/259, 260, 258

(56) References Cited

U.S. PATENT DOCUMENTS

| | | |
|---|---|---|
| 3,615,207 A | 10/1971 | Lee |
| 3,635,841 A | 1/1972 | Keith et al. |
| 3,674,888 A | 7/1972 | Derrien et al. |
| 4,260,840 A | 4/1981 | Puls et al. |
| 4,517,395 A | 5/1985 | Obenaus et al. |
| 4,533,779 A | 8/1985 | Boitaux et al. |
| 4,740,633 A | 4/1988 | Boitaux et al. ............. 568/699 |
| 5,356,851 A | 10/1994 | Sarrazin |
| 5,364,998 A | 11/1994 | Sarrazin |
| 5,475,173 A | 12/1995 | Cheung et al. |
| 5,489,565 A * | 2/1996 | Cheung et al. ............. 502/325 |
| 5,569,802 A | 10/1996 | Luken et al. |
| 5,648,576 A * | 7/1997 | Nguyen Than et al. ..... 585/260 |
| 5,733,839 A * | 3/1998 | Espinoza et al. ........... 502/336 |

FOREIGN PATENT DOCUMENTS

| | | |
|---|---|---|
| DE | 31 19 850 | 2/1982 |
| EP | 87 980 | 9/1983 |
| EP | 211 381 | 2/1987 |
| EP | 523 482 | 1/1993 |
| EP | 653 243 | 5/1995 |
| EP | 722 776 | 7/1996 |
| EP | 780 155 | 6/1997 |

OTHER PUBLICATIONS

DGMK–Conf. Seletive Hydrogenation and Dehydrogenation, Nov. 11 12, 1993, Kassel Germany.
Database WPI Section Ch, Week 199408 Derwent Publications Ltd., London GB; Class H04, AN 1994–057937 OP002127260 & CN 1 071 443 A (Chem Inst Lanzhou Chem Ind Corp), Apr. 28, 1993.
Allman, Selektive Hydrogenation and Purification . . . DGMK, Hamburg, S. 1–30. No Date Available.
Stud. Surf. Sci., Bd 27, 613–666 (1986) Derrien.
Sci & Tech., Biotiaux et al., BD 47, Heft 4, 4/94/141–145. No Date Available.
DGMK–Conf. Selective Hydrodogenation and dehydrogenation, Nov. 11–12, 1993 Kassel, Germany.
Transl. JP 110594/89—Apr. 27, 1989.
Hydrocarbon Processing, Mar. 1985, Boitiaux et al.

* cited by examiner

Primary Examiner—Steven P. Griffin
Assistant Examiner—Christina Ildebrando
(74) Attorney, Agent, or Firm—Keil & Weinkauf

(57) ABSTRACT

Unsaturated compounds in hydrocarbon streams are hydrogenated over a catalyst which, in the unused state, shows reflections which correspond to the following lattice plane spacings in the X-ray diffraction pattern [in $10^{-10}$m]: 4.52, 2.85, 2.73, 2.44, 2.31, 2.26, 2.02, 1.91, 1.80, 1.54, 1.51, 1.49, 1.45 and 1.39 and have specific relative intensities.

16 Claims, No Drawings

CATALYST AND PROCESSES FOR THE SELECTIVE HYDROGENATION OF UNSATURATED COMPOUNDS IN HYDROCARBON STREAMS

The present invention relates to noble metal-containing catalysts on an alumina support and processes for the selective hydrogenation of unsaturated compounds in hydrocarbon streams containing said compounds with the use of these catalysts.

In refineries and petrochemical plants, hydrocarbon streams are produced, stored and processed on a large scale. These hydrocarbon streams frequently contain unsaturated compounds, the presence of which is known to give rise to problems, in particular during processing and/or storage, or which are not the desired product, and which therefore are undesired components of the corresponding hydrocarbon streams. General overviews of such problems in steamcrackers and conventional solutions are given, for example, by H.-M. Allmann, Ch. Herion and P. Polanek in their lecture "Selective Hydrogenations and Purifications in the Steamcracker Downstream Treatment" at the DGMK Conference "Selective Hydrogenation and Dehydrogenation" on Nov. 11 and 12, 1993 in Kassel, Germany, the manuscript of which has also appeared in Conference Report 9305 of DGMK Deutsche Wissenschaftliche Gesellschaft für Erdöl, Erdgas und Kohle e. V., Hamburg, pages 1–30, (ISSN 0938-068X, ISBN 3-928164-61-9), and M. L. Derrien in: L. Cerveny (Editor), Stud. Surf. Sci. Catal., Vol. 27, pages 613–666, Elsevier, Amsterdam 1986.

Usually, the by-product acetylene is undesired in C2 streams of steamcrackers, the by-products propyne and allene are undesired in C3 streams and the by-products 1- and 2-butyne, 1,2-butadiene and vinylacetylene are undesired in C4 streams if 1,3-butadiene is to be obtained as the desired product and further processed, and said by-products and 1,3-butadiene itself where 1-butene, 2-butene (in the cis and/or the trans form) or isobutene are the desired products. In the processing of C5+ streams (C5+: hydrocarbons having at least 5 carbon atoms, pyrolysis gasoline), di- and polyenes, such as pentadiene and cyclopentadiene, alkynes and/or aromatics having unsaturated substituents, such as phenylacetylene and styrene, are undesired in the production and processing of aromatics or carburetor fuel.

In hydrocarbon streams originating from an FCC cracker or reformer instead of a steamcracker, analogous problems occur. A general overview of such problems, especially in the case of C4 and C5+ streams from FCC crackers, is given, for example, by J. P. Boitiaux, C. J. Cameron, J. Cosyns, F. Eschard and P. Sarrazin in their lecture "Selective Hydrogenation Catalysts and Processes: Bench to Industrial Scale" at the DGMK Conference "Selective Hydrogenation and Dehydrogenation" on Nov. 11 and 12, 1993, in Kassel, Germany, the manuscript of which has also appeared in Conference Report 9305 of the DGMK Deutsche Wissenschaftliche Gesellschaft für Erdöl, Erdgas und Kohle e. V., Hamburg, pages 49–57, (ISSN 0938-068X, ISBN 3-928164-61-9).

In general, unsaturated compounds having triple bonds (alkynes) and/or diunsaturated compounds (dienes) and/or other diunsaturated or polyunsaturated compounds (polyenes, allenes, alkynenes) and/or aromatic compounds having one or more unsaturated substituents (phenylalkenes and phenylalkynes) therefore have to be removed from hydrocarbon streams in order to obtain desired products, such as ethylene, propylene, 1-butene, isobutene, 1,3-butadiene, aromatics or carburetor fuel in the required quality. However, not every unsaturated compound is always an undesired component which has to be removed from the hydrocarbon stream in question. For example, 1,3-butadiene, as indicated above, is an undesired by-product or the desired product depending on the application.

The removal of undesired unsaturated compounds from hydrocarbon streams containing them is frequently carried out by selective hydrogenation of some or all of the undesired unsaturated compounds in the corresponding hydrocarbon stream, preferably by selective hydrogenation to give more highly saturated compounds which present no problems and, in a particularly preferred manner, to give components of the hydrocarbon stream which constitute the desired products. For example, acetylene is hydrogenated to ethylene in C2 streams, propyne and allene to propylene in C3 streams, butyne to butenes, vinylacetylene to 1,3-butadiene and/or 1,3-butadiene to butenes in C4 streams and phenylacetylene and styrene to ethylbenzene, cyclopentadiene to cyclopentene and pentadiene to pentene in C5+ streams.

Typically, such compounds have to be removed to residual contents of a few ppm by weight. (Over) hydrogenation to give compounds which are more highly saturated than the desired product and/or the parallel hydrogenation of a desired product containing one or more multiple bonds to give the corresponding more highly or completely saturated compound should however as far as possible be avoided owing to the associated loss of value. The selectivity of the hydrogenation of the undesired unsaturated compounds must therefore be as high as possible. In addition, a sufficiently high activity of the catalyst and a long time-on-stream are generally desirable. At the same time, the catalyst should as far as possible not give rise to any other undesired secondary reactions; for example, catalysis of the isomerization of 1-butene to 2-butene, with the exception of special cases, should as far as possible be avoided. Usually, supported noble metal catalysts in which noble metal is deposited on a catalyst support are used. A frequently used noble metal is palladium and the support is generally a porous inorganic oxide, for example silica, an aluminosilicate, titanium dioxide, zirconium dioxide, zinc aluminate, zinc titanate and/or mixtures of such supports, but alumina or silica is generally used. Furthermore, promoters or other additives may be present. Processes for the selective hydrogenation of unsaturated compounds in hydrocarbon streams containing them are known both in the form of liquid-phase hydrogenation or mixed gas/liquid-phase hydrogenation, by the trickle-bed or liquid-phase procedure, and in the form of pure gas-phase hydrogenation, various process engineering measures for improving the selectivity having been published.

For example, EP-A 87980 describes such a process in a fixed-bed reactor, in which the hydrogen for the hydrogenation is fed in at two or more points along the reactor, with the result that a higher selectivity is achieved. EP-A 523482 discloses carrying out such a process in two reaction zones connected in series, with the result that the undesired overhydrogenation to n-butane is substantially suppressed and the total selectivity also increases. EP-A 81041 states that the addition of carbon monoxide reduces the hydrogenation and isomerization activity of the palladium used as catalyst metal and thus increases the selectivity. JP-A 01-110594 describes the addition of further electron donor compounds, either by doping the catalyst, for example with alkali metals, or by addition to the reaction mixture, for example of alcohols, ethers or nitrogen-containing compounds.

The use of promoters or dopants in addition to the catalyst metal actually having hydrogenation activity is also known. Thus, J. P. Boitiaux, J. Cosyns, M. Derrien and G. Léger in Hydrocarbon Processing, 3 1985, 51–59, describe the use of bimetallic catalysts, in particular those which contain metals of group VIII (current IUPAC nomenclature: groups 8, 9 and 10), especially palladium, and metals of group IB (current IUPAC nomenclature: group 11) of the Periodic Table of Elements. EP-A 564328 and EP-A 564329 describe the use of catalysts which contain metals of group VIII, especially palladium, and metals of group IIIA (current IUPAC nomenclature: group 3), specially indium or gallium, and their use. EP-A 89252 discloses a process for the preparation of a supported catalyst containing palladium and gold and the use of said catalyst. US-A 5,475,173 discloses a catalyst containing palladium, silver and alkali metal fluoride. EP-A 722776 discloses a catalyst which is particularly resistant to contamination with sulfur and which consists of palladium, at least one alkali metal fluoride and optionally silver on an inorganic support, such as $TiO_2$, $ZrO_2$ or preferably $Al_2O_3$. EP-A 211381 describes the use of a catalyst which comprises a metal of group VIII of the Periodic Table of Elements, preferably Pt, at least one metal selected from lead, tin and zinc and an inorganic support. The catalyst preferred there is platinum on a zinc spinel support ($ZnAl_2O_4$). U.S. Pat. No. 4,260,840 describes catalysts which contain palladium and chromium and have a particularly low isomerization tendency.

It is also possible to influence the properties of the catalyst used not only by process engineering measures or the use of specific additives but also by means of the type of support and the manner of distribution of the active material over the internal and external surface of the support.

Thus, DE-A 31 19 850 discloses the use of a catalyst which consists of palladium and silver on an $SiO_2$ support having a BET surface area of from 10 to 200 $m^2/g$ or on an $Al_2O_3$ support having a BET surface area of less than 100 $m^2/g$. DE-A 20 59 978 describes palladium catalysts on an alumina support (alumina is a common synonym for aluminum oxide). The support has a BET surface area of about 120 $m^2/g$ and, before deposition of the palladium, is first subjected to a steam treatment at 110–300° C. and then calcined at 500–1200° C.

In their lecture "The Huls Process for Selective Hydrogenation of Butadiene in crude C4s—Development and Technical Application" at the DGMK Conference "Selective Hydrogenation and Dehydrogenation" on November 11 and 12, 1993, in Kassel, Germany, the manuscript of which has also appeared in the abovementioned Conference Report, pages 31–48, K. H. Walter, W. Droste, D. Maschmeyer and F. Nierlich pointed out the importance of the match between diffusion and reaction rate in the catalyst particle for the process and described catalysts in which palladium is concentrated virtually exclusively on the external surface of the support particles (coated catalysts). EP-A 780155 discloses a catalyst which consists of palladium and a metal of group IB of the Periodic Table of Elements on an $Al_2O_3$ support, at least 80% of the Pd and 80% of the metal of group IB being concentrated in those volume parts of the catalyst particle which are bounded by the radius of the catalyst particle and a distance from the mid point which corresponds to 0.8 times this radius. EP-A 653243 describes a catalyst in which the active components are present predominantly in the meso- and macropores of the support.

EP-A 576828 describes catalysts for the selective hydrogenation of unsaturated compounds in hydrocarbon streams, which consist of noble metal or noble metal compounds on a special $Al_2O_3$ support, the catalyst being defined by a specific X-ray diffraction pattern. This X-ray diffraction pattern is predominantly determined by the support and in this case is typical of the $\eta$-$Al_2O_3$ and/or $\gamma$-$Al_2O_3$ modifications. U.S. Pat Nos. 3,615,207 and 3,635,841 describe palladium catalysts on supports comprising $\delta$- and $\theta$-aluminas which are free of $\alpha$- and $\gamma$-aluminas, and their use for the hydrogenation of alkylanthraquinones.

The requirements as regards the catalysts and processes for the selective hydrogenation of undesired unsaturated compounds in hydrocarbon streams containing said compounds with regard to reducing the residual content of undesired unsaturated compounds after the hydrogenation and to increasing the selectivity are constantly growing. Although the known processes and catalysts already operate at a very high technical level, they are still unsatisfactory in view of the increasing requirements.

It is an object of the present invention to provide an improved catalyst and an improved process for the selective hydrogenation of unsaturated compounds in hydrocarbon streams containing them.

We have found that this object is achieved by a catalyst which comprises at least one metal having hydrogenation activity on an alumina carrier and, in the unused state, shows reflections in the X-ray diffraction pattern which correspond to the following lattice plane spacings:

| Lattice plane spacing d $[10^{-10}$ m] | Relative intensity $I/I_0$ |
| --- | --- |
| 4.52 | 0.05 to 0.1 |
| 2.85 | 0.35 to 0.45 |
| 2.73 | 0.65 to 0.8 |
| 2.44 | 0.45 to 0.55 |
| 2.31 | 0.35 to 0.45 |
| 2.26 | 0.35 to 0.45 |
| 2.02 | 0.45 to 0.6 |
| 1.91 | 0.3 to 0.4 |
| 1.80 | 0.1 to 0.25 |
| 1.54 | 0.25 to 0.35 |
| 1.51 | 0 to 0.35 |
| 1.49 | 0.2 to 0.3 |
| 1.45 | 0.25 to 0.35 |
| 1.39 | 1 |

We have also found a process for the preparation of this catalyst and processes for the selective hydrogenation of unsaturated compounds in hydrocarbon streams containing them with the use of the novel catalyst.

X-ray diffraction patterns are characteristic of the specific structure for the material investigated. The structure of the novel catalyst is sufficiently determined by the occurrence of the abovementioned reflections and differs from that of the known catalysts. In addition to the abovementioned characteristic reflections, one or more reflections of any intensity may occur in the X-ray diffraction pattern for the lattice plane spacings (all in the unit $[10^{-10}$ m]) 3.48, 2.55, 2.38, 2.09, 1.78, 1.74, 1.62, 1.60, 1.57, 1.42, 1.40 and/or 1.37. Furthermore, any further reflections may occur in the X-ray diffraction pattern of the novel catalyst.

Especially in the selective hydrogenation of alkynenes to alkadienes, in the selective hydrogenation of alkynes, alkynenes and alkadienes to alkenes and/or in the selective hydrogenation of phenylalkynes to phenylalkenes and/or phenylalkanes and/or for the selective hydrogenation of phenylalkenes to phenylalkanes, the novel catalyst has excellent properties, in particular a high selectivity when carrying out the process with the starting materials both in the liquid phase or in the mixed liquid and gas phase and in the gas phase. When the novel catalyst is used, the undesired overhydrogenation to the saturated hydrocarbons, for example propane, n-butane or the C5+ alkanes, and the isomerization of 1-butene to 2-butene, which is undesired in the selective hydrogenation of C4 streams, occur only to a surprisingly small extent. In addition, the catalyst is comparatively active and can be operated over comparatively long periods. The novel catalyst also has these advantageous properties without further process engineering measures, for example without the addition of carbon monoxide or alcohols, ethers or nitrogen-containing compounds.

The support consists essentially of alumina which, apart from unavoidable impurities, may also contain a certain amount of other additives, provided that the structure of the catalyst, which is characterized by the abovementioned X-ray diffraction pattern, is not altered thereby. For example, other inorganic oxides, such as oxides of metals of group 2, 3, 4, 13 and 14 of the Periodic Table of Elements may be present, in particular silica, titanium dioxide, zirconium dioxide, zinc oxide, magnesium oxide and calcium oxide. The maximum content of such oxides other than alumina in the support is dependent on the oxide actually present but can in specific cases readily be determined on the basis of the X-ray diffraction pattern, since a change in the structure is associated with a significant change in the X-ray diffraction pattern. In general, the content of such oxides other than alumina is below 50, preferably below 30, particularly preferably below 10, % by weight.

For the preparation of the support, a suitable aluminum-containing raw material, for example boehmite, is peptized with a peptizing agent, such as water, dilute acid or dilute base. The acid used is, for example, a mineral acid, for example nitric acid, or an organic acid, such as formic acid, and the base used is an inorganic base, such as ammonia. The acid or base is in general dissolved in water. A preferably used peptizing agent is water or dilute aqueous nitric acid. The concentration of the nonaqueous fraction of the peptizing agent is in general from 0 to 10, preferably from 0 to 7, particularly preferably from 0 to 5, % by weight. After the peptization, the support is molded and the moldings are then dried and calcined.

Boehmite ($\alpha$-AlO(OH)) is a widely available commercial product but can also be prepared in a known manner immediately before the actual preparation of the support, by precipitation from a solution of an aluminum salt, for example aluminum nitrate, with base, isolation, washing, drying and calcination of the precipitated solid. Advantageously boehmite in the form of a powder is used. A suitable commercial boehmite powder is, for example, Versal® 250, which is obtainable from Euro Support, Amsterdam. The boehmite is treated with the peptizing agent by moistening it with the peptizing agent and thoroughly mixing it, for example in a kneader, mixer or edge mill. The peptization is continued until the material is readily moldable. The material is then molded by means of conventional methods to give the desired support moldings, for example by extrusion, pelleting or agglomeration. Any known method is suitable for molding, if necessary, conventional additives may be used. Examples of such additives are extrusion or pelleting assistants, such as polyglycols or graphite.

It is furthermore possible to mix with the raw support material, prior to molding, additives which, as opening materials, influence the pore structure of the support in a known manner after calcination, for example polymers, fibers, natural opening materials, such as nutshell meals, or other conventional additives. It is preferable to use boehmite in a particle size distribution and to add opening materials which lead to a pore radius distribution of the prepared support in which 50–90% by volume of the total pore volume are in the form of pores having a mean diameter of from 0.01 to 0.1 micrometer and from 10 to 50% by volume of the total pore volume are in the form of pores having a mean diameter of from 0.1 to 1 micrometer. The measures required for this purpose are known to a person skilled in the art.

After molding, the moldings are dried in a conventional manner, in general at above 60° C., preferably above 80° C., particularly preferably above 100° C., for example at from 120° C. to 300° C. The drying is continued until water present in moldings has essentially completely escaped from the moldings, which is generally the case after a few hours. Customary drying times are from one to 30 hours and are dependent on the drying temperature set, a higher temperature reducing the drying time. Drying can be further accelerated by using reduced pressure.

After drying, the moldings are converted into the finished support by calcination. The calcination temperature is from 900° C. to 1100° C., preferably from 950° C. to 1050° C., particularly preferably from 980° C. to 1030° C. The calcination time is in general from 0.5 to 5, preferably from 1 to 4, particularly preferably from 1.5 to 3, hours. The calcination is carried out in a conventional furnace, for example in a rotary furnace, in a belt calciner or a chamber furnace. The calcination can follow the drying directly, without intermediate cooling. The BET surface area of the support thus prepared is usually 30–120 m²/g. The surface area can be varied by known methods (in particular the use of more finely divided or coarser starting materials, calcination time and calcination temperature). The BET surface area is preferably from 40 to 100, particularly preferably from 60 to 90, m²/g. Like the BET surface area, the pore volume, too, can be varied in a known manner; in general, it is from 0.3 to 1.0 ml/g, measured by means of mercury porosimetry. It is preferably from 0.4 to 0.9, particularly preferably from 0.5 to 0.8, ml/g.

After the calcination, the active material and, if required, further additives are deposited on the support thus prepared.

The catalyst may contain one or more metals having hydrogenation activity, additives and/or promoters.

The metals of groups 8, 9 and 10 of the Periodic Table of Elements are particularly suitable as metals having hydrogenation activity in the novel catalyst, in particular ruthenium, rhodium, palladium and/or platinum. Platinum and/or palladium are particularly suitable and palladium is very particularly preferred. The catalyst may furthermore contain all additives and promoters known for catalysts for the selective hydrogenation of polyunsaturated compounds. For example, the novel catalysts may also contain at least one metal from group 11 of the Periodic Table of Elements in addition to the metal or the metals from groups 8, 9 and 10 of the Periodic Table of Elements. In this case, copper and silver are preferred as elements of group 11, silver being particularly preferred. Furthermore, in this case the catalyst very particularly preferably contains palladium and silver.

The metals may be present in pure metallic form but also in the form of compounds, for example in the form of metal oxides. Under the operating conditions of a hydrogenation process, they are present in general in the form of metals. The conversion of any oxides into metals can be effected in a known manner before the use of the catalyst in a hydrogenation process by preliminary reduction and, if required for manipulations with the prereduced catalyst, subsequent surface passivation.

The content of a metal or metals of groups 8, 9 and 10 of the Periodic Table of Elements, in particular palladium, in the catalyst is in general at least 0.05% by weight, based on the total mass of the catalyst, preferably at least 0.08, particularly preferably at least 0.1, % by weight. In general, this content is not more than 2, preferably not more than 1, particularly preferably not more than 0.5, % by weight. Lower or higher contents are possible but are usually economically unsatisfactory owing to excessively low activity or excessively high raw material costs.

For example, the novel catalyst may contain 0.3% by weight of palladium.

The content of the metal or metals of groups other than groups 8, 9 and 10 of the Periodic Table of Elements, in particular metals of group 11, very particularly silver and/or copper, in the catalyst is—if such metals are present—in general at least 0.01% by weight, based on the total mass of the catalyst, preferably at least 0.03, particularly preferably at least 0.05, % by weight. In general, this content is not more than 1, preferably not more than 0.7, particularly preferably not more than 0.5, % by weight. Lower or higher contents are possible but are usually economically unsatisfactory owing to excessively low activity or excessively high material costs.

The ratio of the amount of metal having hydrogenation activity and belonging to groups 8, 9 and 10 of the Periodic Table of Elements to the amount of additives or dopants is a parameter to be optimized in the specific case. If the catalyst contains palladium and silver or copper, the mass ratio of silver or copper to palladium is in general from 0.1 to 5, preferably from 0.15 to 2, particularly preferably from 0.2 to 1. If the catalyst contains palladium and silver and copper, in general both silver and copper are present in a mass ratio relative to palladium of from 0.1 to 5, preferably from 0.15 to 2, particularly preferably from 0.2 to 1.

For example, the novel catalyst may contain 0.2% by weight of palladium and 0.1% by weight of silver.

The metals, additives and/or dopants to be deposited on the support can be applied to the support by any known method, for example by coating from the gas phase (chemical or physical vapor deposition), but the preferred method is impregnation with a solution of the substances and/or compounds to be deposited, which are converted in the course of the further catalyst preparation into the substances to be deposited. The individual substances to be deposited can be deposited individually and/or in portions in a plurality of process steps or together and completely in one process step. Joint deposition in one impregnation stage is preferred. After the impregnation or after the individual impregnation stages, the impregnated support is dried and is converted into the ready-to-use catalyst by calcination and, if required, other known aftertreatment methods (for example activation and subsequent surface passivation).

Impregnation methods for depositing active components, additives and/or dopants on a support are known. In general, the support is impregnated with a solution of salts of the components to be deposited, the volume of the solution being such that the solution is virtually completely absorbed by the pore volume of the support (incipient wetness method). The concentration of the salts in the solution is such that, after impregnation and conversion of the impregnated support into the finished catalyst, the components to be deposited are present in the desired concentration on the catalyst. The salts are chosen so that they do not leave behind any residues which present problems during the catalyst preparation or the subsequent use of the catalyst. In general, nitrates or ammonium salts are used.

The catalyst can, if required, also be prepared in the form of a coated catalyst, and methods for this purpose are known.

In such a case, the active components, additives and/or dopants are preferably predominantly concentrated in a coat which is bounded by the outer surface of the catalyst molding and is not more than 2000, particularly preferably not more than 1000, micrometers thick.

The novel catalyst is preferably prepared with one-stage impregnation of the support by the incipient wetness method using a solution of the nitrates of the metals to be deposited in nitric acid. The concentration of the nitric acid used is at least so high that a clear solution is present. In general, the pH of the solution is not more than 5, preferably not more than 2, particularly preferably not more than 1.

After the impregnation, the impregnated support is dried in a conventional manner, in general at above 60° C., preferably above 80° C., particularly preferably above 100° C., for example at from 120° C. to 300° C. The drying is continued until water present in the impregnated support has essentially completely escaped, which is generally the case after a few hours. Customary drying times are from 1 to 30 hours and are dependent on the drying temperature set, a higher temperature reducing the drying time. The drying can be further accelerated by using reduced pressure.

After the drying, the catalyst is prepared in a conventional manner by calcination. This calcination serves essentially to convert the salts applied by impregnation into the components to be deposited or precursors of such components and differs to this extent from the calcination described above, which serves for the preparation of the support material and the support structure. Where metal nitrates are applied by impregnation, in this calcination essentially the nitrates are decomposed into metals and/or metal oxides, which remain in the catalyst, and nitrous gases, which escape.

The calcination temperature is in general from 250° C. to 900° C., preferably from 280° C. to 800° C., particularly preferably from 300° C. to 700° C. The calcination time is in general from 0.5 to 20, preferably from 0.5 to 10, particularly preferably from 0.5 to 5, hours. The calcination is carried out in a conventional furnace, for example in a rotary furnace, in a belt calciner or in a chamber furnace. The calcination can be carried out directly after the drying, without intermediate cooling of the impregnated and dried support.

After the calcination, the catalyst is in principle ready for use. If required or desired, it is activated in a known manner by preliminary reduction and, if required, also surface-passivated before it is used for the selective hydrogenation.

The novel processes for the selective hydrogenation are distinguished by the use of the novel catalyst. The novel hydrogenation processes using the novel catalyst are generally carried out in exactly the same way as the known hydrogenation processes under heterogeneous catalysis which serve the same purposes. They can be carried out as gas-phase processes under heterogeneous catalysis, in which both the hydrocarbon stream and the hydrogen for hydrogenation are present in the gas phase, or as gas/liquid-phase processes under heterogeneous catalysis, in which the hydrocarbon stream is present at least partly in the liquid phase and hydrogen is present in the gas phase and/or in dissolved form in the liquid phase. The parameters to be set, such as throughput of hydrocarbon stream, expressed as space velocity in the unit $[m^3/m^3*h]$, based on the catalyst volume, temperature and pressure, are chosen analogously to those of the known processes. The temperature is usually from 0° C. to 180° C. and the pressure from 2 to 50 bar.

The amount of hydrogen used, based on the amount of hydrocarbon stream fed in, is dependent on the content of undesired unsaturated compounds in the hydrocarbon stream and on the type of said compounds. In general, the hydrogen is added in an amount of from 0.8 to 5, preferably from 0.95 to 2, times the amount required stoichiometrically for complete hydrogen conversion on passage through the reactor. The hydrogenation of triple bonds usually takes place more rapidly than that of the conjugated double bonds, and this in turn more rapidly than that of the unconjugated double bonds. This permits corresponding control of the process on the basis of the added amount of hydrogen. In special cases, for example if a high degree of isomerization of 1-butene to cis- or trans-2-butene is desired, it is known that it is also possible to use a larger excess of hydrogen, for example a ten-fold hydrogen excess. The hydrogen may contain inert substances, for example noble gases, such as helium, neon or argon, other inert gases, such as nitrogen, carbon dioxide and/or lower alkanes, for example methane, ethane, propane and/or butane. Such inert gases in the hydrogen are preferably present in a concentration of less than 30% by volume. Preferably, the hydrogen is free of carbon monoxide.

The processes can be carried out in one reactor or in a plurality of reactors connected in parallel or in series, in each case in a single path or by a circulation procedure. When the processes are carried out in the gas/liquid phase, the hydrocarbon stream, after passage through a reactor, is usually freed from gases in a separator and a part of the liquid obtained is recycled to the reactor. The ratio of recycled hydrocarbon stream to hydrocarbon stream fed into the reactor for the first time, i.e. the reflux ratio, is set so that the desired conversion is achieved under the other reaction conditions, such as pressure, temperature, throughput and amount of hydrogen.

The intended uses of the novel processes are, for example, the hydrogenation of alkynenes to alkadienes, of alkynes, alkynenes and alkadienes to alkenes, of phenylalkynes to phenylalkenes and/or of phenylalkenes to phenylalkanes.

Examples of novel processes are those:

for the selective hydrogenation of acetylene in C2 streams to ethylene with-minimum formation of ethane (referred to below as process A for simplification), for the selective hydrogenation of propyne and/or propadiene in C3 streams to propylene with minimum formation of propane (process B), for the selective hydrogenation of 1-butyne, 2-butyne, 1,2-butadiene and/or vinylacetylene in C4 streams to 1,3-butadiene, 1-butene, cis-2-butene and/or trans-2-butene (process C), for the selective hydrogenation of 1-butyne, 2-butyne, 1,2-butadiene, 1,3-butadiene and/or vinylacetylene in C4 streams to 1-butene, cis-2-butene and/or trans-2-butene, in the case of butadiene-rich C4 streams (crude C4 cut) or low-butadiene C4 streams (refined product I) (process D), and for the selective hydrogenation of unsaturated compounds and/or unsaturated substituents of aromatic compounds in C5+ streams to more highly saturated compounds and/or aromatic compounds having more highly saturated substituents, with minimum hydrogenation of the aromatic nuclei (process E), in each case with the use of the novel catalyst.

Process A is usually carried out as a gas-phase process with a space velocity of the gaseous C2 stream of from 500 $m^3/m^3*h$, based on the catalyst volume, to 10,000 $m^3/m^3*h$ at from 0° C. to 250° C. and from 0.01 to 50 bar, one mole of hydrogen being added per mole of acetylene in the C2 stream.

Process B is usually carried out as a gas-phase process or as a gas/liquid-phase process with a space velocity of the liquid C3 stream of from 1 $m^3/m^3*h$, based on the catalyst volume, to 50 $m^3/m^3*h$ at from 0° C. to 180° C. and from 0.01 to 50 bar, from one to two moles of hydrogen being added per mole of propyne and propadiene in the C3 stream.

Process C is usually carried out as a gas/liquid-phase process with a space velocity of the liquid C4 stream of from 1 $m^3/m^3*h$, based on the catalyst volume, to 50 $m^3/m^3*h$ at from 0° C. to 180° C. and from 2 to 50 bar, from one to two moles of hydrogen being added per mole of butyne, 1,2-butadiene and vinylacetylene in the C4 stream. Process C can be used, for example, as a selective so-called front end-vinylacetylene hydrogenation before a butadiene extraction.

Process D is usually carried out as a one-stage or two-stage gas/liquid-phase process with a space velocity of the liquid C4 stream of from 0.1 $m^3/m^3*h$, based on the catalyst volume, to 60 $m^3/m^3*h$, preferably from 1 to 50 $m^3/m^3*h$, at a reactor inlet temperature of from 20° C. to 90° C., preferably from 20° C. to 700° C., and a pressure of from 5 to 50, preferably from 10 to 30, bar, one mole of hydrogen being added per mole of butyne, butadiene and vinylacetylene in the C4 stream. For example, the process is carried out in two stages, the butadiene content, which is from 20 to 80% by weight, based on the total stream, in typical C4 streams from steamcrackers, being reduced to a content of from 0.1 to 20% by weight in the first stage and to the desired residual content of from a few ppm by weight to about 1% by weight in the second stage. It is also possible to distribute the total reaction over more than two reactors, for example three or four. The individual reaction stages can be operated with partial recycling of the hydrocarbon stream, and the reflux ratio is usually from 0 to 30. When process D is carried out, isobutene is obtained essentially unchanged and can be separated from the C4 stream by known methods before or after process D is carried out. Process D can be used, for example, as a butadiene hydrogenation in the C4 stream (if butadiene is not to be obtained as the desired product) or as the selective so-called tail-end vinylacetylene hydrogenation after the butadiene extraction from the C4 stream.

Process E is preferably carried out as a gas/liquid-phase process with a space velocity of the liquid C5+ stream of from 0.5 $m^3/m^3*h$, based on the catalyst volume, to 30 $m^3/m^3*h$ at from 0° C. to 180° C. and from 2 to 50 bar, from one to two moles of hydrogen being added per mole of bond to be hydrogenated in the C5+ stream. Process E can be carried out, for example, as a selective hydrogenation of pyrolysis gas, as a selective hydrogenation of olefins in reformate streams or coke furnace condensates, for the hydrogenation of phenylacetylene to styrene or for the hydrogenation of styrene to ethylbenzene.

EXAMPLES

All X-ray diffraction data stated were measured with a Siemens diffractometer, type D 5000, using Cu-$K_\alpha$ radiation. The measuring range for 2θ was from 10° to 70°, corresponding to a lattice plane spacing range of from $5 \cdot 10^{-10}$ m to $1.35 \cdot 10^{-10}$ m. The accuracy of the values obtained for the lattice plane spacings is $\pm 0.02 \cdot 10^{-10}$ m The conversion C with respect to butadiene, butenyne and butyne, the selectivities and the 1-butene retention (a measure of the isomerization activity of the catalyst) are defined as follows:

$U=[x_S(1,3\text{-butadiene})+x_S(1,2\text{-butadiene})+x_S(1\text{-butyne})+ x_S(\text{butenyne}) -x_P(1,3\text{-butadiene})x-_P(1,2\text{-butadiene})x-$ $_P$(1-butyne)x$_{-P}$(butenyne)]/[x$_S$(1,3-butadiene)+x$_S$(1,2-butadiene)+x$_S$(1-butyne)+x$_S$(butenyne)]

Total butene selectivity $S_{TB}$=1-{[x$_P$(n-butane)–x$_S$(n-butane)]/[x$_S$(1,3-butadiene)+x$_S$(1,2-butadiene)+x$_S$(1-butyne)+x$_S$(butenyne)x$_{-P}$(1,3-butadiene)x$_{-P}$(1,2-butadiene)x$_{-P}$(1-butyne)x$_{-P}$(butenyne)]}

1-butene selectivity $S_{1B}$=[x$_P$(1-butene)–x$_S$(1-butene)]/[x$_S$(1,3-butadiene)+x$_S$(1,2-butadiene)+x$_S$(1-butyne)+x$_S$(butenyne)–x$_P$(1, 3-butadiene)x$_{-P}$(1,2-butadiene)x$_{-P}$(1-butyne)x$_{-P}$(butenyne)]

1-butene retention $R_{1B}$=1+{[x$_P$(1-butene)–x$_S$(1-butene)]/[x$_S$(1-butene)]}, where x$_S$(A) is the mass fraction of component A in the starting material and x$_P$(A) is the mass fraction of component A in the product.

Comparative Examples and Examples 1 to 8

Catalyst and Process for the Liquid-phase Hydrogenation of Crude C4 Cut From a Steamcracker (Process D, Butadiene-rich C4 Stream)

Comparative Example 1

Preparation of Comparative Catalyst 1

In a mixer, boehmite (Versal® 250, obtained from Euro Support, Amsterdam) was moistened with water, thoroughly worked in an edge mill until the material was readily moldable and then extruded to give 3 mm extrudates. Thereafter, the extrudates were dried for 2 hours at 120° C. and calcined for 4hours at 1200° C. The extrudates were then impregnated with a solution of Pd(NO$_3$)$_2$ in HNO$_3$ (pH=1.3) by the incipient wetness method. The impregnated support was then dried for 12 hours at 120° C. and calcined for 6 hours at 330° C. The palladium content of the finished catalyst was 0.3% by weight and its bulk density was 1150 g/l. Compared with the novel catalyst, the support of comparative catalyst 1 was calcined for too long and at excessively high temperatures.

The catalyst had the following X-ray diffraction pattern (only lines with I/I$_0$≧5% are shown):

| Lattice plane spacing d [10$^{-10}$ m] | Relative intensity I/I$_0$ |
|---|---|
| 3.48 | 0.45 |
| 2.55 | 0.83 |
| 2.38 | 0.34 |
| 2.08 | 1 |
| 1.74 | 0.46 |
| 1.60 | 0.99 |
| 1.51 | 0.09 |
| 1.40 | 0.37 |
| 1.38 | 0.52 |

Comparative Example 2

Preparation of Comparative Catalyst 2

In a mixer, 70% by weight of boehmite (Versal® 250, obtained from Euro Support, Amsterdam) and 30% by weight of α-Al$_2$O$_3$ powder (type CT 3000 SG from Alcoa) were moistened with water, thoroughly orked in an edge mill until the material was readily moldable and then extruded to give 3 mm extrudates. Thereafter, the extrudates were dried for 2 hours at 120° C. and calcined for 2 hours at 900° C. The extrudates were then impregnated with an aqueous solution of Pd(NO$_3$)$_2$ in nitric acid (pH=0.2) by the incipient wetness method. The impregnated support was then dried for 12 hours at 120° C. and calcined for 6 hours at 330° C. The palladium content of the finished catalyst was 0.3% by weight and its bulk density was 890 g/l. Compared with the novel catalyst, he support of comparative catalyst 1 was calcined for an insufficient time and at excessively low temperatures.

The catalyst had the following x-ray diffraction pattern (only lines with I/I$_0$≧5% are shown):

| Lattice plane spacing d [10$^{-10}$ m] | Relative intensity I/I$_0$ |
|---|---|
| 3.48 | 0.48 |
| 2.84 | 0.06 |
| 2.72 | 0.08 |
| 2.55 | 0.86 |
| 2.44 | 0.09 |
| 2.38 | 0.43 |
| 2.31 | 0.07 |
| 2.28 | 0.07 |
| 2.09 | 1 |
| 2.02 | 0.08 |
| 1.99 | 0.10 |
| 1.97 | 0.08 |
| 1.74 | 0.49 |
| 1.60 | 0.96 |
| 1.55 | 0.08 |
| 1.54 | 0.06 |
| 1.52 | 0.10 |
| 1.51 | 0.14 |
| 1.40 | 0.50 |
| 1.39 | 0.19 |
| 1.37 | 0.62 |

Comparative Example 3

Preparation of Comparative Catalyst 3

A commercially available Al$_2$O$_3$ support (Spheralite 508F from Rhône-Poulenc) was impregnated with an aqueous solution of Pd(NO$_3$)$_2$ in nitric acid (pH=0.2) by the incipient wetness method. Thereafter, the impregnated support was dried for 12 hours at 120° C. and calcined for 6 hours at 330° C. The palladium content of the finished catalyst was 0.3% by weight and its bulk density was 640 g/l. Comparative catalyst 3 corresponds roughly to the catalysts disclosed in DE-A 20 59 978.

The catalyst had the following X-ray diffraction pattern (only lines with I/I$_0$≧5% are shown):

| Lattice plane spacing d [10$^{-10}$ m] | Relative intensity I/I$_0$ |
|---|---|
| 4.55 | 0.07 |
| 2.73 | 0.25 |
| 2.43 | 0.35 |
| 2.28 | 0.35 |
| 1.99 | 0.63 |
| 1.95 | 0.40 |
| 1.79 | 0.10 |
| 1.53 | 0.21 |
| 1.41 | 0.67 |
| 1.39 | 1 |

Example 4

(According to the Invention): Preparation of Catalyst 4

In a mixer, boehmite (Versal® 250, obtained from Euro Support, Amsterdam) was moistened with water, thoroughly worked in an edge mill until the material was readily moldable and then extruded to give 3 mm extrudates. Thereafter, the extrudates were dried for 2 hours at 120° C. and calcined for 2 hours at 1000° C. The extrudates were then impregnated with a solution of $Pd(NO_3)_2$ in $HNO_3$ (pH=0.5) by the incipient wetness method. Thereafter, the impregnated support was dried for 12 hours at 120° C. and calcined for 6 hours at 330° C. The palladium content of the finished catalyst was 0.3% by weight and its bulk density was 620 g/l.

The catalyst had the following X-ray diffraction pattern (only lines with $I/I_0 \geq 5\%$ are shown):

| Lattice plane spacing d $[10^{-10}$ m$]$ | Relative intensity $I/I_0$ |
| --- | --- |
| 5.47 | 0.05 |
| 4.54 | 0.10 |
| 3.48 | 0.27 |
| 2.85 | 0.38 |
| 2.73 | 0.68 |
| 2.55 | 0.62 |
| 2.44 | 0.47 |
| 2.38 | 0.39 |
| 2.31 | 0.39 |
| 2.26 | 0.35 |
| 2.09 | 0.62 |
| 2.02 | 0.48 |
| 1.91 | 0.33 |
| 1.80 | 0.15 |
| 1.74 | 0.33 |
| 1.60 | 0.56 |
| 1.54 | 0.28 |
| 1.51 | 0.20 |
| 1.49 | 0.23 |
| 1.45 | 0.32 |
| 1.40 | 0.71 |
| 1.39 | 1 |
| 1.38 | 0.49 |

Carrying Out the Experiments for the Liquid-phase Hydrogenation of Crude C4 Cut From a Steamcracker The experiments were carried out in a pilot plant which was equipped with an electrically heatable fixed-bed reactor of 16 mm diameter and 2 m length, a preheater, a separator, a condenser for the reactor discharge and a liquid circulation. The amount of catalyst used was 200 ml. The crude C4 cut was metered in via a feed pump and mixed, at a mixing point, with the hydrogen fed in with flow control. In the separator, the reactor discharge was separated into gas and liquid phase, and the gas phase was discarded. The major part of the liquid phase was recycled to the reactor. A smaller portion corresponding to the amount of crude C4 cut fed to the reactor for the first time was removed continuously from the separator as product. The analyses were carried out by means of a gas chromatograph.

Before the hydrocarbon was fed to the reactor for the first time, the catalysts were treated with hydrogen for 12 hours at 120° C. and 5 bar. The plant was then filled with selectively hydrogenated C4 cut, heated to 60° C and put into operation, and crude C4 cut and hydrogen were fed in after the operating conditions had been achieved (pressure, temperature, throughput).

The throughput through the reactor, expressed as space velocity of liquid hydrocarbon stream fed for the first time to the reactor (fresh feed), was 9.0 $m^3/m^3$ per h, and the temperature of the fresh feed was set at 60° C. by means of the preheater. The reflux ratio was adjusted so that the temperature increase in the reactor was from 20 to 50° C. The reflux ratios set in each case are shown below. The pressure was 15±1 bar and the molar ratio of added hydrogen to butadiene present in the crude C4 cut was brought to from 1.00 to 1.02.

Comparative Example 5

Hydrogenation Using Comparative Catalyst 1

The reflux ratio was 8.2 and the compositions of crude C4 cut and hydrogenated product were:

|  | C4 cut | Product |
| --- | --- | --- |
| Butadiene + butenyne + butyne [% by weight] | 43.7 | 1.1 |
| 1-butene [% by weight] | 14.3 | 36.3 |
| trans-2-butene [% by weight] | 4.5 | 20.3 |
| cis-2-butene [% by weight] | 3.3 | 7.3 |
| isobutene [% by weight] | 23.7 | 23.8 |
| isobutane [% by weight] | 3.0 | 3.0 |
| n-butane [% by weight] | 7.2 | 7.8 |
| C5 hydrocarbons [% by weight] | 0.3 | 0.4 |

Comparative Example 6

Hydrogenation Using Comparative Catalyst 2

The reflux ratio was 11 and the compositions of the crude C4 cut and hydrogenated product were:

|  | C4 cut | Product |
| --- | --- | --- |
| Butadiene + butenyne + butyne [% by weight] | 43.2 | 1.3 |
| 1-butene [% by weight] | 14.4 | 38.4 |
| trans-2-butene [% by weight] | 4.4 | 19.0 |
| cis-2-butene [% by weight] | 3.0 | 5.7 |
| isobutene [% by weight] | 23.9 | 23.8 |
| isobutane [% by weight] | 3.0 | 3.1 |
| n-butane [% by weight] | 8.0 | 8.6 |
| C5 hydrocarbons [% by weight] | 0.1 | 0.1 |

Comparative Example 7

Hydrogenation Using Comparative Catalyst 3

The reflux ratio was 8.2 and the compositions of crude C4 cut and hydrogenated product were:

|  | C4 cut | Product |
| --- | --- | --- |
| Butadiene + butenyne + butyne [% by weight] | 43.7 | 1.5 |
| 1-butene [% by weight] | 14.3 | 38.4 |
| trans-2-butene [% by weight] | 4.5 | 19.7 |
| cis-2-butene [% by weight] | 3.3 | 6.1 |
| isobutene [% by weight] | 23.6 | 23.6 |
| isobutane [% by weight] | 2.9 | 2.9 |
| n-butane [% by weight] | 7.2 | 7.4 |
| C5 hydrocarbons [% by weight] | 0.5 | 0.4 |

Example 8

Hydrogenation Using Catalyst 4

The reflux ratio was 8.2 and the compositions of crude C4 cut and hydrogenated product were:

|  | C4 cut | Product |
| --- | --- | --- |
| Butadiene + butenyne + butyne [% by weight] | 46.3 | 1.5 |
| 1-butene [% by weight] | 15.3 | 41.6 |
| trans-2-butene [% by weight] | 5.1 | 20.4 |
| cis-2-butene [% by weight] | 3.8 | 6.6 |
| isobutene [% by weight] | 23.9 | 23.9 |
| isobutane [% by weight] | 1.0 | 1.0 |
| n-butane [% by weight] | 4.4 | 4.5 |
| C5 hydrocarbons [% by weight] | 0.2 | 0.5 |

Discussion of the Comparative Examples and Examples 1–8

The conversions and selectivities achieved in the hydrogenation experiments have the following values, in mol%:

|  | C | $S_{TB}$ | $S_{1B}$ |
| --- | --- | --- | --- |
| Comparative catalyst 1 | 97.5 | 98.6 | 51.6 |
| Comparative catalyst 2 | 97.0 | 98.6 | 57.3 |
| Comparative catalyst 3 | 96.6 | 99.5 | 57.1 |
| Catalyst 4 | 96.8 | 99.8 | 58.7 |

Comparative catalyst 1 gives an unsatisfactory total butene selectivity and by far the lowest and completely unsatisfactory 1-butene selectivity. Comparative catalyst 2 likewise gives an unsatisfactory total butene selectivity with minimally lower conversion, but a significantly higher, although not yet satisfactory, 1-butene selectivity. Comparative catalyst 3 gives a very substantially improved total butene selectivity and the same 1-butene selectivity with minimally lower conversion. The novel catalyst 4 gives a further improved total butene selectivity and a substantially improved 1-butene selectivity for a comparable conversion. With the novel catalyst, both the undesired overhydrogenation to n-butane is suppressed to the greatest extent and the desired product 1-butene is obtained in the best yield.

Comparative Examples and Examples 9 to 14

Catalyst and Process for the Liquid-phase Hydrogenation of a C4 Stream From a Steamcracker After a Butadiene Extraction (Process D, Low-butadiene C4 Stream)

Comparative Example 9

Preparation of Comparative Catalyst 5

Example 1 from EP-A 653243 was reworked, but the palladium content was brought to 0.3% by weight. The catalyst had a bulk density of 380 g/l.

The catalyst had the following X-ray diffraction pattern (only lines with $I/I_0 \geq 5\%$ are shown):

| Lattice plane spacing d $[10^{-10}$ m] | Relative intensity $I/I_0$ |
| --- | --- |
| 2.64 | 0.43 |
| 2.42 | 0.56 |
| 2.29 | 0.50 |
| 1.97 | 0.67 |
| 1.52 | 0.34 |
| 1.40 | 1 |

Comparative Example 10

Preparation of Comparative Catalyst 6

A commercially available $Al_2O_3$ support (Spheralite 508F from Rhône-Poulenc) was impregnated with an aqueous solution of $Pd(NO_3)_2$ and $AgNO_3$ in nitric acid (pH=0.2) by the incipient wetness method. Thereafter, the impregnated support was dried for 12 hours at 120° C. and calcined for 6 hours at 330° C. The palladium content of the prepared catalyst was 0.2% by weight, its silver content was 0.1% by weight and its bulk density was 640 g/l. Comparative catalyst 3 corresponds roughly to the catalysts disclosed in DE-A 31 19 850.

The catalyst had the following X-ray diffraction pattern (only lines with $I/I_0 \geq 5\%$ are shown):

| Lattice plane spacing d $[10^{-10}$ m] | Relative intensity $I/I_0$ |
| --- | --- |
| 4.50 | 0.06 |
| 2.74 | 0.23 |
| 2.43 | 0.37 |
| 2.28 | 0.35 |
| 1.99 | 0.64 |
| 1.95 | 0.42 |
| 1.79 | 0.11 |
| 1.52 | 0.24 |
| 1.40 | 0.76 |
| 1.39 | 1 |

Example 11

(According to the Invention): Preparation of Catalyst

In a mixer, boehmite (Versal® 250, obtained from Euro Support, Amsterdam) was moistened with water, thoroughly worked in an edge mill until the material was readily moldable and then extruded to give 3 mm extrudates. Thereafter, the extrudates were dried for 2 hours at 120° C. and calcined for 2 hours at 1000° C. The extrudates were then impregnated with an aqueous solution of $Pd(NO_3)_2$ and $AgNO_3$ in nitric acid (pH=0.5) by the incipient wetness method. Thereafter, the impregnated support was dried for 12 hours at 120° C. and calcined for 6 hours at 330° C. The palladium content of the prepared catalyst was 0.2% by weight, its silver content was 0.1% by weight and its bulk density was 620 g/l.

The catalyst had the following X-ray diffraction pattern (only lines with $I/I_0 \geq 5\%$ are shown):

| Lattice plane spacing d $[10^{-10}$ m] | Relative intensity $I/I_0$ |
|---|---|
| 5.47 | 0.05 |
| 4.54 | 0.10 |
| 3.48 | 0.27 |
| 2.85 | 0.38 |
| 2.73 | 0.68 |
| 2.55 | 0.62 |
| 2.44 | 0.47 |
| 2.38 | 0.39 |
| 2.31 | 0.39 |
| 2.26 | 0.35 |
| 2.09 | 0.62 |
| 2.02 | 0.48 |
| 1.91 | 0.33 |
| 1.80 | 0.15 |
| 1.74 | 0.33 |
| 1.60 | 0.56 |
| 1.54 | 0.28 |
| 1.51 | 0.20 |
| 1.49 | 0.23 |
| 1.45 | 0.32 |
| 1.40 | 0.71 |
| 1.39 | 1 |
| 1.38 | 0.49 |

Carrying Out the Experiments for the Liquid-phase Hydrogenation of a C4 Stream from a Steamcracker, After Butadiene Extraction The experiments were carried out in the pilot plant described before Example 5 and already used for the experiments for the liquid-phase hydrogenation of crude C4 cut, in the same way as the experiments of Examples 5 to 8, except that a C4 stream (refined product I) freed from butadiene by a conventional extraction method was used instead of crude C4 cut, that the space velocity was 15 m³/m³ per h and the pressure was 12 bar (except in Example 14: 9 bar) and that the ratio of hydrogen to butadiene differed and is stated in the individual examples. This ratio was set so that a butadiene conversion of 99.8%, corresponding to a residual butadiene content of 10 ppm, resulted under the other reaction conditions. The reflux ratio was brought to 1.0 in all cases; it is substantially lower in these experiments than in experiments 5 to 8, since substantially less heat of hydrogenation is produced.

Comparative Example 12

Hydrogenation Using Comparative Catalyst

The molar ratio of hydrogen to butadiene in the refined product I was 5.2, and the compositions of refined product I and hydrogenated product were:

|  | Refined product I | Product |
|---|---|---|
| Butadiene + butenyne + butyne [% by weight] | 0.53 | 0.001 |
| 1-butene [% by weight] | 27.0 | 11.0 |
| trans-2-butene [% by weight] | 10.0 | 18.7 |
| cis-2-butene [% by weight] | 5.2 | 11.2 |
| isobutene [% by weight] | 42.8 | 42.6 |
| isobutane [% by weight] | 3.1 | 3.0 |
| n-butane [% by weight] | 11.0 | 13.2 |
| C5 hydrocarbons [% by weight] | 0.4 | 0.3 |

Comparative Example 13

Hydrogenation Using Comparative Catalyst

The molar ratio of hydrogen to butadiene in the refined product I was 2.9 and the compositions of refined product I and hydrogenated product were:

|  | C4 cut | Product |
|---|---|---|
| Butadiene + butenyne + butyne [% by weight] | 0.43 | 0.001 |
| 1-butene [% by weight] | 25.1 | 20.8 |
| trans-2-butene [% by weight] | 7.8 | 10.2 |
| cis-2-butene [% by weight] | 5.4 | 7.2 |
| isobutene [% by weight] | 42.3 | 42.2 |
| isobutane [% by weight] | 4.8 | 4.6 |
| n-butane [% by weight] | 14.0 | 14.8 |
| C5 hydrocarbons [% by weight] | 0.2 | 0.2 |

Example 14

Hydrogenation Using Catalyst 7

The molar ratio of hydrogen to butadiene in the refined product I was 1.4 and the compositions of refined product I and hydrogenated product were:

|  | C4 cut | Product |
|---|---|---|
| Butadiene + butenyne + butyne [% by weight] | 0.55 | 0.001 |
| 1-butene [% by weight] | 23.9 | 23.4 |
| trans-2-butene [% by weight] | 8.1 | 8.7 |
| cis-2-butene [% by weight] | 5.7 | 6.0 |
| isobutene [% by weight] | 43.6 | 43.7 |
| isobutane [% by weight] | 4.5 | 4.4 |
| n-butane [% by weight] | 13.5 | 13.6 |
| C5 hydrocarbons [% by weight] | 0.15 | 0.2 |

Discussion of the Comparative Examples and Examples 9–14

The conversions, total butene selectivities and values for the 1-butene retention, in mol%, achieved in the hydrogenation experiments and the increase in n-butane $I_{nB}$, a measure of the overhydrogenation, in % by weight, have the following values:

|  | C | $S_{TB}$ | $R_{1B}$ | $I_{nB}$ |
|---|---|---|---|---|
| Comparative catalyst 5 | 99.8 | −310 | 40.6 | 2.2 |
| Comparative catalyst 6 | 99.8 | −91 | 82.8 | 0.8 |
| Catalyst 7 | 99.8 | 76 | 98.0 | 0.1 |

Comparative catalyst 5 has comparatively low 1-butene retention and a comparatively high overhydrogenation of 2.2% by weight to n-butane. Comparative catalyst 6 has a substantially higher but nevertheless unsatisfactory 1-butene retention and substantially reduced but nevertheless unsatisfactory overhydrogenation with the same conversion. The novel catalyst 7 on the other hand has good selectivity and a low level of overhydrogenation.

Example 15

Process for Removing Butadiene From Crude C4 Cut by Selective Two-stage Liquid-phase Hydrogenation (Process D, Butadiene-rich C4 Stream)

Crude C4 cut was hydrogenated in the pilot plant described before Example 5 and in the manner described there but with a space velocity of 9.0 m³ per m³ per h, and a reflux ratio of 8.2 and at 60° C. and 15 bar and with a molar ratio of hydrogen to butadiene contained in the crude C4 stream of 1.00, using catalyst 4. The product was then hydrogenated in a further plant which differed from the first one through a lack of recycling, in the same manner but with a space velocity of 15 m³ per m³ per h, at 60° C. and 9 bar and with a molar ratio of hydrogen to butadiene contained in the product of the first stage of 1.4, using catalyst 7.

The compositions of crude C4 cut and products were:

| [% by weight] | C4 cut | 1st stage | 2nd stage |
| --- | --- | --- | --- |
| Butadiene + butenyne + butyne | 46.3 | 0.48 | 0.001 |
| 1-butene | 15.3 | 39.5 | 38.7 |
| trans-2-butene | 5.1 | 22.4 | 23.0 |
| cis-2-butene | 3.8 | 7.7 | 8.3 |
| isobutene | 23.9 | 23.9 | 23.9 |
| isobutane | 1.0 | 1.0 | 1.0 |
| n-butane | 4.4 | 4.7 | 4.8 |
| C5 hydrocarbons | 0.2 | 0.3 | 0.3 |

Over both stages, a conversion C of 99.8%, a selectivity $S_{TB}$ of 99.1% and a selectivity $S_{1B}$ of 50.5% with an n-butane formation $I_{nB}$ of 0.4% were achieved.

We claim:

1. A catalyst which comprises at least one metal having hydrogenation activity on an alumina carrier and, in the unused state, shows reflections in the X-ray diffraction pattern which correspond to the following lattice plane spacings:

| Lattice plane spacing d [$10^{-10}$ m] | Relative intensity $I/I_o$ |
| --- | --- |
| 4.52 | 0.05 to 0.1 |
| 2.85 | 0.35 to 0.45 |
| 2.73 | 0.65 to 0.8 |
| 2.44 | 0.45 to 0.55 |
| 2.31 | 0.35 to 0.45 |
| 2.26 | 0.35 to 0.45 |
| 2.02 | 0.45 to 0.6 |
| 1.91 | 0.3 to 0.4 |
| 1.80 | 0.1 to 0.25 |
| 1.54 | 0.25 to 0.35 |
| 1.51 | 0 to 0.35 |
| 1.49 | 0.2 to 0.3 |
| 1.45 | 0.25 to 0.35 |
| 1.39 | 1 |

2. A catalyst as claimed in claim 1, which, in the unused state, shows at least one additional reflection in the X-ray diffraction pattern which corresponds to one of the following lattice plane spacings [in $10^{-10}$ m]: 3.48, 2.55, 2.38, 2.09, 1.78, 1.74, 1.62, 1.60, 1.57, 1.42, 1.40 and 1.37.

3. A catalyst as claimed in claim 1, the metal having hydrogenation activity or the metals having hydrogenation activity being a metal or metals from group 8, 9 or 10 of the Periodic Table of Elements.

4. A catalyst as claimed in claim 1, the metal having hydrogenation activity being platinum and/or palladium.

5. A catalyst as claimed in claim 4, the metal having hydrogenation activity being palladium and being contained in an amount of at least 0.05% by weight and not more than 2% by weight, based on the total weight of the catalyst.

6. A catalyst as claimed in claim 1, the catalyst comprising at least one metal of group 11 of the Periodic Table of Elements in addition to the metal having hydrogenation activity.

7. A catalyst as claimed in claim 6, the metal of group 11 of the Periodic Table of Elements being copper and/or silver.

8. A catalyst as claimed in claim 7, the metal of group 11 being silver and being contained in an amount of at least 0.01% by weight and not more than 1% by weight, based on the total weight of the catalyst.

9. A process for the preparation of a catalyst described in claim 1 by treating an aluminum-containing raw material with water, dilute acid or dilute base, shaping to give moldings, drying the moldings, calcining the dried moldings, impregnating the calcined moldings with solution containing the at least one metal having hydrogenation activity to be deposited, drying the impregnated moldings and finishing the catalyst by calcining the impregnated and dried moldings, wherein the dried moldings are calcined at above 900° C. and below 1100° C.

10. A process as claimed in claim 9, wherein the dried moldings are calcined over a period of at least 0.5 hour and not more than 5 hours.

11. A process for the selective hydrogenation of unsaturated compounds in hydrocarbon streams in the gas or liquid phase at from 0° C. to 180° C. and from 2 to 50 bar, wherein the selective hydrogenation is carried out in one or more reaction stages, comprising contacting the hydrocarbon stream with the catalyst described in claim 1 in at least one reaction stage.

12. A process as claimed in claim 11, wherein acetylene in a C2 stream is hydrogenated selectively to ethylene.

13. A process as claimed in claim 11, wherein propyne and/or propadiene in a C3 stream are hydrogenated selectively to propylene.

14. A process as claimed in claim 11, wherein 1-butyne, 2-butyne, 1,2-butadiene and/or vinylacetylene in a C4 stream are hydrogenated selectively to 1,3-butadiene, 1-butene, cis-2-butene and/or trans-2-butene.

15. A process as claimed in claim 11, wherein 1-butyne, 2-butyne, 1,2-butadiene, 1,3-butadiene and/or vinylacetylene in a C4 stream are hydrogenated selectively to 1-butene, cis-2-butene and/or trans-2-butene.

16. A process as claimed in claim 11, wherein unsaturated compounds and/or unsaturated substituents of aromatic compounds in a C5+ stream are hydrogenated selectively to more highly saturated compounds and/or aromatic compounds having more highly saturated substituents.

* * * * *